(12) United States Patent
Kontani (10) Patent No.: US 8,718,420 B2
(45) Date of Patent: May 6, 2014

(54) SPR SENSOR CELL AND SPR SENSOR

(75) Inventor: Tomohiro Kontani, Osaka (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 13/702,855

(22) PCT Filed: Jun. 2, 2011

(86) PCT No.: PCT/JP2011/062729
§ 371 (c)(1),
(2), (4) Date: Dec. 7, 2012

(87) PCT Pub. No.: WO2011/158660
PCT Pub. Date: Dec. 22, 2011

(65) Prior Publication Data
US 2013/0077912 A1 Mar. 28, 2013

(30) Foreign Application Priority Data

Jun. 15, 2010 (JP) .................................. 2010-136230
May 11, 2011 (JP) .................................. 2011-106561

(51) Int. Cl.
*G02B 6/00* (2006.01)

(52) U.S. Cl.
USPC .......................................................... 385/12

(58) Field of Classification Search
USPC .......................................................... 385/12
See application file for complete search history.

(56) References Cited

U.S. PATENT DOCUMENTS

| 6,432,364 B1 * | 8/2002 | Negami et al. ............. 422/82.11 |
| 2008/0218736 A1 * | 9/2008 | Shaw .............................. 356/72 |
| 2008/0218761 A1 | 9/2008 | Nishikawa et al. |

FOREIGN PATENT DOCUMENTS

| JP | 200019100 A | 1/2000 |
| JP | 2000019100 A | 1/2000 |
| JP | 2007033203 A | 2/2007 |
| JP | 20070033203 A | 2/2007 |
| JP | 2008216055 A | 9/2008 |

OTHER PUBLICATIONS

ISA Japan, International Search Report of PCT/JP2011/062729, Aug. 9, 2011, WIPO, 2 pages.
International Bureau of WIPO, International Preliminary Report on Patentability of PCT/JP2011/062729, Jan. 3, 2013, Switzerland, 5 pages.
International Bureau of WIPO, Translation of International Preliminary Report on Patentability of PCT/JP2011/062729, Jan. 24, 2013, Switzerland, 6 pages.

* cited by examiner

*Primary Examiner* — Jerry Blevins
(74) *Attorney, Agent, or Firm* — Alleman Hall McCoy Russell & Tuttle LLP (57) ABSTRACT

An SPR sensor cell is an SPR sensor cell including an optical waveguide to be brought into contact with a sample. The optical waveguide includes an under clad layer, a core layer provided in the under clad layer such that at least a part thereof is exposed from the under clad layer, and a metal particle layer covering the core layer exposed from the under clad layer to be brought into contact with the sample.

4 Claims, 4 Drawing Sheets

SPR SENSOR CELL AND SPR SENSOR

TECHNICAL FIELD

The present invention relates to an SPR sensor cell and an SPR sensor, and particularly to an SPR sensor cell including an optical waveguide and an SPR sensor including the SPR sensor cell.

BACKGROUND ART

Conventionally, in the fields of chemical analysis, biochemical analysis, and the like, an SPR sensor (Surface Plasmon Resonance) sensor including an optical fiber has been used.

In the SPR sensor including the optical fiber, a metal thin film is formed on the outer peripheral surface of the tip portion of the optical fiber, while an analysis sample is fixed thereto, and light is introduced into the optical fiber. Of the introduced light, light at a specified wavelength causes surface plasmon resonance in the metal thin film to attenuate the light intensity thereof.

In such an SPR sensor, the wavelength which causes the surface plasmon resonance normally differs depending on the refractive index of the analysis sample fixed to the optical fiber.

Therefore, if the wavelength at which the light intensity attenuates after the occurrence of the surface plasmon resonance is measured, the wavelength that has caused the surface plasmon resonance can be specified. Also, if the wavelength at which the attenuation occurs has changed and is detected, it is possible to confirm that the wavelength which causes the surface plasmon resonance has changed. This allows a change in the refractive index of the analysis sample to be confirmed.

Consequently, such an SPR sensor can be used for various chemical analyses and biochemical analyses such as, e.g., measurement of the concentration of a sample and detection of an immune reaction.

For example, when the sample is a solution, the refractive index of the sample (solution) depends on the concentration of the solution. Accordingly, in the SPR sensor in which the sample (solution) is brought into contact with a metal thin film, by measuring the refractive index of the sample (solution), the concentration of the sample can be detected and, by also confirming that the refractive index thereof has changed, it can be confirmed that the concentration of the sample (solution) has changed.

In the analysis of an immune reaction, e.g., an antibody is fixed onto the metal thin film of the optical fiber in the SPR sensor via a dielectric film and a specimen is brought into contact with the antibody, while surface plasmon resonance is caused. At this time, if an immune reaction occurs between the antibody and the specimen, the refractive index of the sample changes. Therefore, by confirming that there is a change between the refractive indices of the sample before and after the contact between the antibody and the specimen, it can be determined that the immune reaction has occurred between the antibody and the specimen.

However, in an SPR sensor including such an optical fiber, the tip portion of the optical fiber has a minute cylindrical shape resulting in the problem that it is difficult to form a metal thin film and fix an analysis sample.

To solve the problem, an SPR sensor cell has been proposed which includes, e.g., a core through which light is transmitted and a clad covering the core. At a predetermined position in the clad, a through hole is formed to reach the surface of the core, and a metal thin film is formed on the surface of the core at a position corresponding to the through hole (see, e.g., Patent Document 1 shown below).

The SPR sensor cell allows easy formation of the metal thin film for causing surface plasmon resonance on the surface of the core and easy fixation of the analysis sample to the surface thereof.

PRIOR ART DOCUMENT

Patent Document

Patent Document 1: Japanese Unexamined Patent No. 2000-19100

SUMMARY OF THE INVENTION

Problems to be Solved by the Invention

However, in the SPR sensor cell described in Patent Document 1 mentioned above, on the upper surface of the core facing the through hole of the clad, the metal thin film is formed. In such a form, there is a limit to the sensitivity of detecting the concentration of the analysis sample, a change therein, or the like.

An object of the present invention is to provide an SPR sensor cell and an SPR sensor each having an excellent detection sensitivity.

Means for Solving the Problem

An SPR sensor cell of the present invention includes an optical waveguide to be brought into contact with a sample, wherein the optical waveguide includes an under clad layer, a core layer provided in the under clad layer such that at least a part thereof is exposed from the under clad layer, and a metal particle layer covering the core layer exposed from the under clad layer to be brought into contact with the sample.

In the SPR sensor cell of the present invention, it is preferable that the metal particle layer covers 15 to 60% of a surface area of the core layer exposed from the under clad layer.

In the SPR sensor cell of the present invention, it is preferable that an average particle size of metal particles forming the metal particle layer is in a range of 5 to 300 nm.

In the SPR sensor cell of the present invention, it is preferable that the optical waveguide further includes an over clad layer formed on the under clad layer so as to surround the sample in contact with the metal particle layer.

An SPR sensor of the present invention includes the SPR sensor cell described above.

Effect of the Invention

The SPR sensor cell and the SPR sensor each according to the present invention can achieve an improvement in detection sensitivity.

EMBODIMENT OF THE INVENTION

Figure 1:
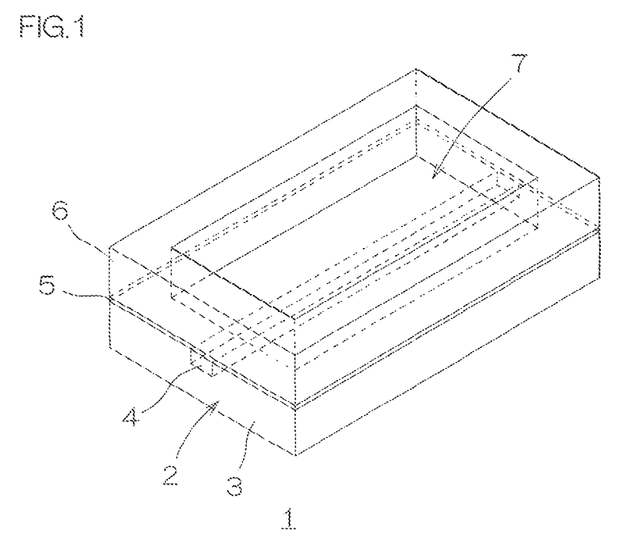
FIG. 1 is a perspective view showing an embodiment of an SPR sensor cell of the present invention.
Figure 2:
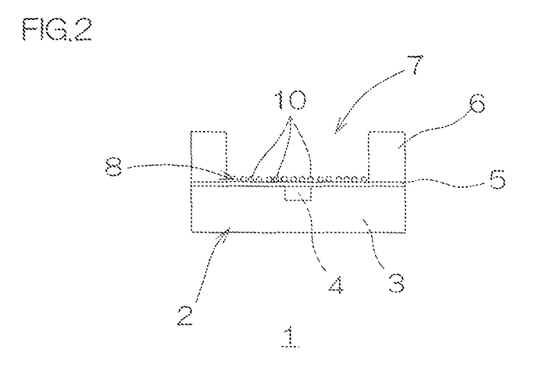
FIG. 2 is a cross-sectional view of the SPR sensor cell shown in FIG. 1.

FIG. 1 is a perspective view showing an embodiment of an SPR sensor cell of the present invention. FIG. 2 is a cross-sectional view of the SPR sensor cell shown in FIG. 1.

As shown in FIGS. 1 and 2, an SPR sensor cell 1 is formed in the shape of a bottomed frame which is generally rectangular in plan view, and includes an optical waveguide 2. In the SPR sensor cell 1, a sample to be analyzed by an SPR sensor 11 (described later) is placed. In the SPR sensor 11, a support member (not shown) which supports the optical waveguide 2 can be provided as necessary. Note that, in the following description of the SPR sensor cell 1, when a direction is mentioned, the state where the sample is placed in the SPR sensor cell 1 is used as a reference in an up-down direction. That is, in FIG. 1, the upper side on a paper surface is defined as an upper side, and the lower side on a paper surface is defined as a lower side.

In the present embodiment, the SPR sensor cell itself 1 serves as the optical waveguide 2, and the optical waveguide includes an under clad layer 3, a core layer 4, a protective layer 5, and an over clad layer 6.

The under clad layer 3 is formed in the shape of a flat plate which is generally rectangular in plan view and has a predetermined thickness in the up-down direction.

The core layer 4 is formed in a generally rectangular columnar shape (specifically, a rectangular cross-sectional shape which flattens in a widthwise direction) extending in a direction perpendicular to each of the widthwise direction (direction perpendicular to a thickness direction, which similarly applies to the following) of the under clad layer 3 and the thickness direction thereof. The core layer 4 is embedded in the upper end portion of the widthwise generally middle portion of the under clad layer 3. Note that, in the following description of the SPR sensor cell 1, the direction in which the core layer 4 extends is defined as a propagation direction in which light propagates in the optical waveguide 2.

The core layer 4 is disposed such that both surfaces thereof in the propagation direction are flush with the both surfaces of the under clad layer 3 in the propagation direction and the upper surface thereof is flush with the upper surface of the under clad layer 3. That is, the core layer 4 has the upper surface thereof exposed from the under clad layer 3.

When the core layer 4 is embedded in the under clad layer 3 such that the upper surface thereof is flush with the upper surface of the under clad layer 3, in the formation of a metal particle layer 8 (described later), metal particles 10 (described later) can be efficiently placed only on the upper side of the core layer 4.

To both end portions of the core layer 4 in the propagation direction, a light source 12 (described later) and a light measuring device 13 (described later) are optically connected.

As necessary, the protective layer 5 is formed as a thin layer having the same shape as that of the under clad layer 3 in plan view so as to cover the entire upper surfaces of the under clad layer 3 and the core layer 4.

If the protective layer 5 is formed, when the sample is, e.g., liquid, it is possible to prevent the core layer 4 from being swelled by the sample.

The over clad layer 6 is formed in a rectangular frame shape in plan view on the protective layer 5 such that the outer perimeter thereof is generally the same as the outer perimeter of the under clad layer 3 when viewed in plan view.

Accordingly, the optical waveguide 2 is formed in a bottomed frame shape having the protective layer 5 formed over the under clad layer 3 and the core layer 4 as the bottom wall thereof and having the over clad layer 6 as the sidewalls thereof. The portion surrounded by the protective layer 5 and the over clad layer 6 is defined as a sample container 7 which contains the sample therein.

In such an optical waveguide 2, the sample container 7 is provided with a metal particle layer 8.

Figure 3:
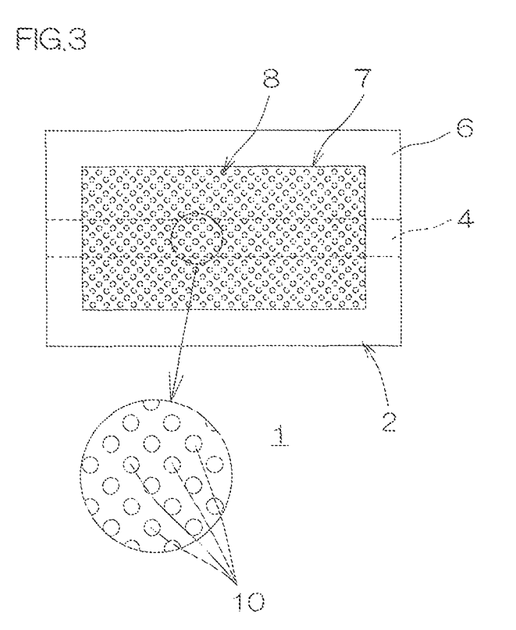
FIG. 3 is an illustrative view for illustrating a metal particle layer provided in the SPR sensor cell shown in FIG. 1.

As shown in FIGS. 2 and 3, the metal particle layer 8 is formed in the sample container 7 so as to uniformly cover the protective layer 5. That is, the metal particle layer 8 is formed so as to uniformly cover the upper surface of the core layer 4.

FIGS. 4(a)-4(f) are process views showing a production method of the SPR sensor cell shown in FIG. 1.

Next, a production method of the SPR sensor cell 1 is described with reference to FIGS. 4(a)-4(f).

Figure 4A:
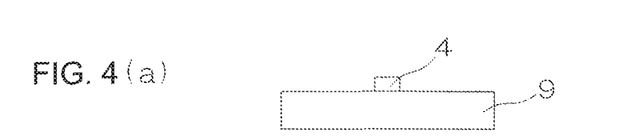
FIG. 4(a) is a process view showing a production method of the SPR sensor cell shown in FIG. 1, showing the step of forming a core layer on a substrate.

In the method, as shown in FIG. 4(a), a substrate 9 having a flat plate shape is prepared first. Then, on the substrate 9, the core layer 4 is formed.

The substrate 9 is formed of a ceramic material such as, e.g., silicon or glass, a metal material such as, e.g., copper, aluminum, stainless steel, or an iron alloy, a resin material such as, e.g., polyimide, glass-epoxy, or polyethylene terephthalate (PET), or the like. Preferably, the substrate 9 is formed of the ceramic material. The thickness of the substrate 9 is in a range of, e.g., 10 to 5000 μm, or preferably 10 to 1500 μm.

Examples of a material for forming the core layer 4 include resin materials such as, e.g., polyimide resin, polyamide resin, silicone resin, epoxy resin, acrylic resin, fluorine-modified products thereof, deuterium-modified products thereof, a modified product of fluorine, and the like. Preferably, such a resin material is blended with a photosensitive agent to be used as a photosensitive resin.

To form the core layer 4, a varnish (resin solution) of the resin shown above is prepared, applied in the foregoing pattern to the surface of the substrate 9, dried, and cured as necessary. When the photosensitive resin is used, a varnish thereof is applied to the entire surface of the substrate 9, dried, exposed to light via a photomask, subjected to post-exposure heating as necessary, and developed into a pattern, which is then heated.

The thickness of the core layer 4 thus formed is in a range of, e.g., 5 to 100 μm, and the width thereof is in a range of, e.g., 5 to 100 μm. The refractive index of the core layer 4 is in a range of, e.g., not less than 1.44 and not more than 1.65.

Figure 4B:
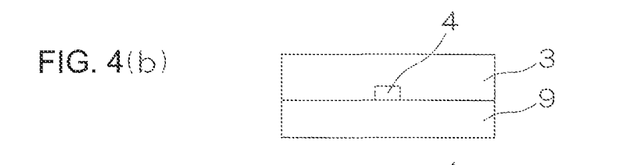
FIG. 4(b) is a process view showing a production method of the SPR sensor cell shown in FIG. 1, showing the step of forming an under clad layer on the substrate so as to cover the core layer.

Next, in the method, as shown in FIG. 4(b), the under clad layer 3 is formed in the pattern described above on the substrate 9 so as to cover the core layer 4.

Examples of a material for forming the under clad layer 3 include a resin material which is prepared from the same resin material as shown above so as to have a refractive index adjusted to be lower than the refractive index of the core layer 4.

To form the under clad layer 3 on the substrate 9, e.g., a varnish (resin solution) of the resin shown above is prepared, applied onto the substrate 9 by, e.g., casting, a spin coater, or the like so as to cover the core layer 4, then dried, and heated as necessary. When the photosensitive resin is used, a varnish thereof is applied, dried, then exposed to light via a photomask, subjected to post-exposure heating as necessary, developed, and then heated.

The thickness of the under clad layer 3 thus formed which is measured from the surface of the core layer 4 is in a range of, e.g., 5 to 200 μm. The refractive index of the under clad layer 3 is set lower than the refractive index of the core layer 4 to be in a range of, e.g., not less than 1.42 and less than 1.55.

Thus, the under clad layer 3 and the core layer 4 are formed flush at the lower surfaces thereof in contact with the substrate 9.

Figure 4C:
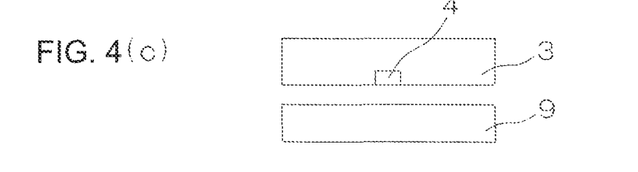
FIG. 4(c) is a process view showing a production method of the SPR sensor cell shown in FIG. 1, showing the step of stripping the substrate from the core layer and the under clad layer.

Next, in the method, as shown in FIG. 4(c), the substrate 9 is stripped from the under clad layer 3 and the core layer 4, and the under clad layer 3 and the core layer 4 are turned upside down.

As a result, the surfaces of the under clad layer 3 and the core layer 4 that have been in contact with the substrate 9 are exposed as the upper surfaces.

Figures 4D, 4E:
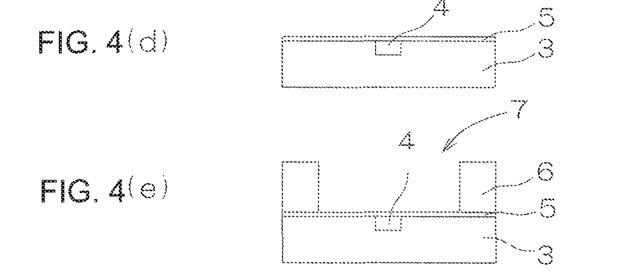
FIG. 4(d) is a process view showing a production method of the SPR sensor cell shown in FIG. 1, showing the step of forming a protective layer on the core layer and the under clad layer each exposed by the stripping of the substrate.
FIG. 4(e) is a process view showing a production method of the SPR sensor cell shown in FIG. 1, showing the step of forming an over clad layer on the surface of the protective layer.

Next, in the method, as shown in FIG. 4(d), the protective layer 5 is formed on the under clad layer 3 and the core layer 4.

Examples of a material of forming the protective layer 5 include silicon dioxide, aluminum oxide, and the like. Preferably, a material which is obtained from such a material so as to have a refractive index adjusted to be lower than the refractive index of the core layer 4 is used.

Examples of a method for forming the protective layer 5 include a sputtering method, a vapor deposition method, and the like. Preferably, the sputtering method is used.

The thickness of the protective layer 5 thus formed is in a range of, e.g., 1 to 100 nm, or preferably 5 to 20 nm. The refractive index of the protective layer 5 is set lower than the refractive index of the core layer 4 to be in a range of, e.g., not less than 1.25 and less than 1.55.

Next, in the method, as shown in FIG. 4(e), the over clad layer 6 is formed in the pattern described above on the protective layer 5.

As a material for forming the over clad layer 6, the same resin material as that of the under clad layer 3 shown above is used.

To form the over clad layer 6, e.g., a sheet having a rectangular frame shape in plan view is formed from the material shown above in advance and then laminated as the over clad layer 6 on the protective layer 5.

Note that, when the over clad layer 6 is laminated on the protective layer 5, it is also possible to treat the surface of the protective layer 5 with a known primer such as a silane coupling agent in advance, and then laminate the over clad layer 6 thereon. If the surface of the protective layer 5 is treated with the primer shown above, when the metal particle layer 8 is formed, the metal particles 10 (described later) can be solidly fixed to the protective layer 5.

As the silane coupling agent, an amino-group-containing silane coupling agent such as γ-aminopropyl triethoxy silane can be used.

When the treatment is performed using the silane coupling agent as the primer, e.g., an alcohol solution of the silane coupling agent is applied to the protective layer 5 and then subjected to heat treatment.

To form the over clad layer 6, e.g., it is also possible that a varnish (resin solution) of the resin shown above is prepared, applied in the pattern described above to the surface of the protective layer 5, dried, and then cured as necessary. When a photosensitive resin is used, it is also possible that a varnish is applied to the entire surface of the protective layer 5, dried, then exposed to light via a photomask, subjected to post-exposure heating as necessary, then developed into a pattern, and subsequently heated.

The thickness of the over clad layer 6 thus formed is in a range of, e.g., 5 to 200 μm, or preferably 25 to 100 μm. The refractive index of the over clad layer 6 is set lower than the refractive index of the core layer 4. For example, the refractive index of the over clad layer 6 is set similarly to, e.g., the refractive index of the under clad layer 3. Note that, when the refractive index of the protective layer 5 is lower than the refractive index of the core layer 4, the refractive index of the over clad layer 6 need not necessarily be lower than the refractive index of the core layer 4.

In such an over clad layer 6, the size and shape of the sample container 7 are not particularly limited, and are determined appropriately in accordance with the type and use purpose of the sample. When the SPR sensor cell 1 is to be reduced in size, the sample container 7 is preferably formed small.

Figure 4F:
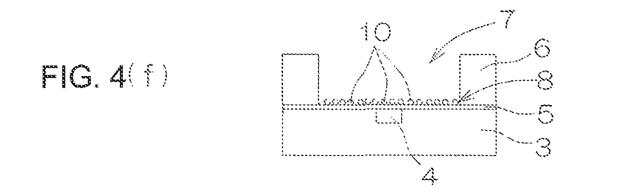
FIG. 4(f) is a process view showing a production method of the SPR sensor cell shown in FIG. 1, showing the step of forming a metal particle layer on the surface of the protective layer exposed from the over clad layer so as to cover the core layer.

Next, in the method, as shown in FIG. 4(f), the metal particle layer 8 is formed in the sample container 7 so as to cover the core layer 4.

Examples of the metal particles 10 forming the metal particle layer 8 include particles made of a metal such as gold, silver, copper, aluminum, or platinum, particles obtained by covering the surfaces of inorganic particles of silica, carbon black, or the like with any of the metals shown above, particles obtained by covering the surfaces of organic particles of a resin or the like with any of the metals shown above, and the like. Preferably, the particles made of the metal are used or, more preferably, gold particles are used.

The average particle size of the metal particles 10 is calculated as, e.g., an average value of any 100 particles observed by electron microscopic observation, and is in a range of, e.g., 5 to 300 nm, or preferably 10 to 150 nm.

When the average particle size of the metal particles 10 is less than 5 nm, a signal intensity (intensity of light transmitted through the SPR sensor cell 1) may decrease. On the other hand, when the average particle size of the metal particles 10 exceeds 300 nm, the sensitivity of detection may decrease.

To form the metal particle layer 8, e.g., the metal particles 10 mentioned above are dispersed in a known solvent to prepare a particle-dispersed liquid, and the particle-dispersed liquid is applied to the protective layer 5 and dried.

Note that a gold-particle-dispersed liquid in which gold particles are dispersed as the metal particles 10 is commercially available. For example, EMGC Series (available from British BioCell International Ltd.) or the like can be used.

In the metal particle layer 8 thus formed, the individual metal particles 10 are preferably not stacked on each other in the thickness direction, but are formed as a single particle layer. The individual metal particles 10 are disposed in slightly spaced-apart and mutually independent relation so as not to come in contact with each other.

In plan view, the metal particle layer 8 covers, e.g., 15 to 60%, preferably 20 to 50% of the surface area of the core layer 4 exposed from the under clad layer 3 (see the enlarged view of FIG. 3).

When the metal particle layer 8 covers the core layer 4 exposed from the under clad layer 3 in the proportion (coverage) shown above, the metal particle layer 8 is formed as a single particle layer in which almost all the metal particles 10 are independently disposed, and therefore the concentration of the sample, a change therein, or the like can be more accurately detected. Note that the coverage of the metal particle layer 8 to the inner area of the sample container 7 is also the same as described above.

When the metal particle layer 8 covers the core layer 4 exposed from the under clad layer 3 in a proportion (coverage) less than that shown above, the signal intensity may decrease. On the other hand, when the metal particle layer 8 covers the core layer 4 exposed from the under clad layer 3 in a proportion (coverage) in excess of that shown above, it may be difficult to form the metal particle layer 8 as a single particle layer in which the metal particles 10 are independently disposed to result in a lower detection sensitivity.

In this manner, the SPR sensor cell 1 can be produced. In the SPR sensor cell 1, the sample is contained (placed) in the sample container 7 to be brought into contact with the metal particle layer 8. That is, the sample is surrounded by the over clad layer 6 in the sample container 7.

According to the SPR sensor cell 1, the concentration of the sample, a change therein, or the like can be accurately detected.

Since the over clad layer 6 is formed so as to surround the sample in contact with the metal particle layer 8, the sample can be easily placed on the surface of the metal particle layer 8, and therefore an improvement in workability can be achieved.

Figure 5:
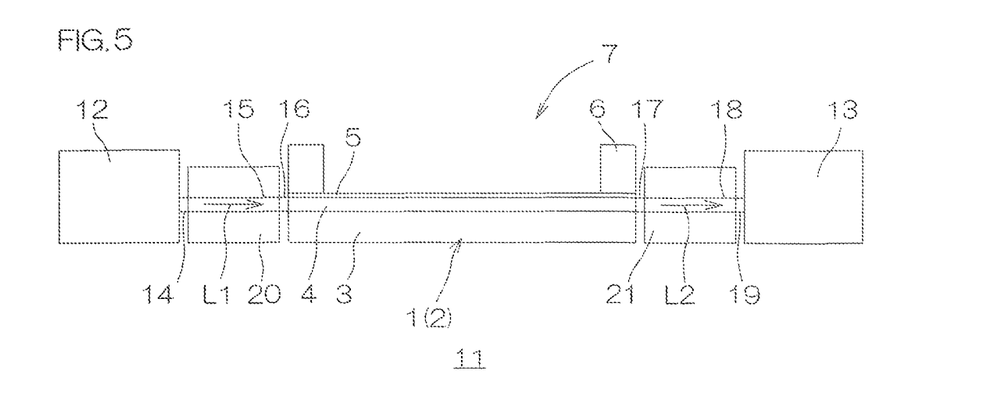
FIG. 5 is a schematic side cross-sectional view showing an embodiment of the SPR sensor of the present invention.

FIG. 5 is a schematic side cross-sectional view showing an embodiment of the SPR sensor of the present invention.

Next, the SPR sensor 11 including the SPR sensor cell 1 is described with reference to FIG. 5.

As shown in FIG. 5, the SPR sensor 11 includes the light source 12, the light measuring device 13, and the SPR sensor cell 1 described above.

The light source 12 is a known light source such as, e.g., a white light source or a monochromatic light source, which is connected to a light-source-side optical fiber 15 via a light-source-side optical connector 14. The light-source-side optical fiber 15 is connected to one end portion of the SPR sensor cell 1 (core layer 4) in the propagation direction via a light-source-side optical fiber block 16.

To the other end portion of the SPR sensor cell 1 (core layer 4) in the propagation direction, a measuring-device-side optical fiber 18 is connected via a measuring-device-side optical fiber block 17. The measuring-device-side optical fiber 18 is connected to the light measuring device 13 via a measuring-device-side optical connector 19.

The light measuring device 13 is connected to a known arithmetic processor (not shown) to allow data to be displayed, stored, and processed.

In such an SPR sensor 11, the SPR sensor cell 1 is fixed by a known sensor cell fixing device (not shown). The sensor cell fixing device (not shown) is configured to be movable along a predetermined direction (i.e., the widthwise direction of the SPR sensor cell 1), so that the SPR sensor cell 1 is disposed at any position.

The light-source-side optical fiber 15 is fixed to a light-source-side optical fiber fixing device 20. The measuring-device-side optical fiber 18 is fixed to a measuring-device-side optical fiber fixing device 21.

The light-source-side optical fiber fixing device 20 and the measuring-device-side optical fiber fixing device 21 are fixed onto a known 6-axis movable stage (not shown), and are configured to be movable in the propagation direction of the optical fibers, the widthwise direction (direction horizontally perpendicular to the propagation direction) thereof, the thickness direction (direction vertically perpendicular to the propagation direction) thereof, and directions (three directions) of rotation around the respective directions (three directions).

According to such an SPR sensor 11, the light source 12, the light-source-side optical fiber 15, the SPR sensor cell 1 (core layer 4), the measuring-device-side optical fiber 18, and the light measuring device 13 can be arranged on one axis, and light can be introduced from the light source 12 so as to pass therethrough.

In the SPR sensor 11, the SPR sensor cell 1 described above is used to allow the concentration of the sample, a change therein, or the like to be accurately detected.

A description is given below to an application of the SPR sensor 1.

In the application, e.g., the sample is contained (placed) first in the sample container 7 of the SPR sensor cell 1 shown in FIG. 5 to be brought into contact with the metal particle layer 8. Then, from the light source 12, predetermined light is introduced into the SPR sensor cell 1 (core layer 4) via the light-source-side optical fiber 15 (see the arrow L1 shown in FIG. 5).

The light introduced into the SPR sensor cell 1 (core layer 4) passes through the SPR sensor cell 1 (core layer 4), while repeating total internal reflection in the core layer 4, and a part of the light incident on the metal particle layer 8 on the upper surface of the core layer 4 via the protective layer 5 is attenuated by surface plasmon resonance.

Thereafter, the light transmitted through the SPR sensor cell 1 (core layer 4) is introduced into the light measuring device 13 via the measuring-device-side optical fiber 18 (see the arrow L2 shown in FIG. 5).

That is, in the SPR sensor 11, of the light introduced into the light measuring device 13, the light intensity at a wavelength which has caused the surface plasmon resonance in the core layer 4 is attenuated.

Since the wavelength which causes the surface plasmon resonance depends on the refractive index of the sample contained (placed) in the SPR sensor cell 1 and the like, by detecting the attenuation of the light intensity of the light introduced into the light measuring device 13, a change in the refractive index of the sample can be detected.

More specifically, when, e.g., a white light source is used as the light source 12, the wavelength at which the light intensity is attenuated after the light transmission through the SPR sensor cell 1 (wavelength which causes the surface plasmon resonance) is measured by the light measuring device 13 and, if the wavelength at which the attenuation occurs has changed and is detected, it is possible to confirm the change in the refractive index of the sample.

Alternatively, when, e.g., a monochromatic light source is used as the light source 12, a change in (the degree of attenuation of) the light intensity of monochromatic light after being transmitted through the SPR sensor cell 1 is measured by the light measuring device 13 and, if the degree of attenuation has changed and is detected, in the same manner as described above, it is possible to confirm that the wavelength which causes the surface plasmon resonance has changed and confirm the change in the refractive index of the sample.

Accordingly, such an SPR sensor 11 can be used for various chemical analyses and biochemical analyses such as, e.g., measurement of the concentration of a sample and detection of an immune reaction based on a change in the refractive index of the sample.

More specifically, when, e.g., the sample is a solution, the refractive index of the sample (solution) depends on the concentration of the solution. Accordingly, if the refractive index of the sample (solution) is detected in the SPR sensor 11 in which the sample (solution) has been brought into contact with the metal particle layer 8, the concentration of the sample can be measured. In addition, if the refractive index of the sample (solution) has changed and is detected, it is possible to confirm that the concentration of the sample (solution) has changed.

In the detection of an immune reaction, e.g., an antibody is fixed onto the metal particle layer 8 of the SPR sensor cell 1 via a dielectric film and a specimen is brought into contact with the antibody. At this time, if an immune reaction occurs between the antibody and the specimen, the refractive index of the sample changes. Therefore, by detecting a change existing between the refractive indices of the sample before and after the contact between the antibody and the specimen, it can be determined that the immune reaction has occurred between the antibody and the specimen.

According to such an SPR sensor cell 1 and an SPR sensor 11, with a simple configuration, an improvement in detection sensitivity can be achieved.

Note that, in the embodiment described above, one core layer 4 is formed in the SPR sensor cell 1, but the number of the core layers 4 is not particularly limited. It is also possible to form a plurality of the core layers 4 in widthwise mutually spaced-apart relation.

When the optical waveguide 2 includes the plurality of core layers 4, by the SPR sensor 11 including the SPR sensor cell 1, samples can be simultaneously analyzed a plurality of times. As a result, the efficiency of analysis can be improved.

In the embodiment described above, the core layer 4 is formed in a generally rectangular columnar shape, but the shape of the core layer 4 is not particularly limited. The core layer 4 can be formed into any shape such as, e.g., a generally semicircular shape (semicircular columnar shape) in cross section or a generally convex shape (convex columnar shape) in cross section.

Also, in the embodiment described above, the metal particle layer 8 is formed in the sample container portion 7 so as to cover the entire protective layer 5, but the metal particle layer 8 can also be formed only over the core layer 4 so as to cover at least the core layer 4.

In the embodiment described above, the upper end portion of the SPR sensor cell 1 is open, but the upper end portion of the SPR sensor cell 1 can also be provided with a lid covering the sample container 7. This can prevent the sample from coming into contact with outside air during measurement.

It is also possible to provide the lid covering the sample container 7 with an inlet for injection of the sample (liquid) into the sample container 7 and an outlet for ejection of the sample from the sample container 7, inject the sample from the inlet, allow the sample to pass through the inside of the sample container 7, and eject the sample from the outlet. This allows the physical properties of the sample to be sequentially measured, while allowing the sample to flow in the sample container 7.

EXAMPLES

While in the following, the present invention will be described more specifically with reference to Examples and Comparative Example, the present invention is not limited thereto.

Example 1

On a silicon substrate (substrate), using a photosensitive epoxy resin, a core layer having a generally rectangular columnar shape having a thickness of 50 µm and a width of 50 µm was formed (see FIG. 4(a)).

Next, on the silicon substrate, an under clad layer was formed using a photosensitive epoxy resin having a refractive index lower than that of the photosensitive epoxy resin used to form the core layer so as to cover the core layer and have a thickness of 100 µm which is measured from the upper surface of the core layer (see FIG. 4(b)).

Next, from the under clad layer and the core layer, the silicon substrate was stripped (see FIG. 4(c)), and the under clad layer and the core layer were turned upside down.

Then, on the under clad layer and the core layer, a silicon dioxide thin film having a thickness of 10 nm was formed as a protective layer by a sputtering method (see FIG. 4(d)).

Subsequently, a 3 mass % ethanol solution of γ-aminopropyl triethoxy silane (silane coupling agent) was applied onto the protective layer and then subjected to heat treatment at 100° C. for 2 hours.

Then, a silicon rubber sheet formed with an opening having a length of 1 mm in a widthwise direction and a length of 6 mm in a propagation direction was separately prepared and laminated as an over clad layer on the protective layer (see FIG. 4(e)). Thus, a sample container having a length of 1 mm in the widthwise direction and a length of 6 mm in the propagation direction was defined.

Then, the gold-particle-dispersed liquid (EMGC Series available from British BioCell International Ltd.) shown in the following Table 1 was adjusted to a predetermined concentration, applied to the protective layer in the sample container, and dried. Subsequently, to remove gold particles unattached to the protective layer, the protective layer in the sample container was washed with ethanol, so that a metal particle layer was formed on the protective layer (see FIG. 4(f)).

In this manner, an SPR sensor cell was obtained. The following Table 1 shows the average particle size of the gold particles and their coverage (the proportion of the area covered with the metal particle layer in plan view to the surface area of the core layer exposed from the under clad layer).

Examples 2 to 25

SPR sensor cells were obtained in the same manner as in Example 1 except that each of the gold-particle-dispersed liquids shown in the following Table 1 was applied to the protective layer in the sample container. In the following Table 1, the average particle size of the gold particles and the coverage thereof in each of the Examples are shown.

Comparative Example

An SPR sensor cell was obtained in the same manner as in Example 1 described above except that, instead of applying the gold-particle-dispersed liquid, a thin film having a thickness of 50 nm was formed on the protective layer in the sample container by vapor-depositing gold.

Evaluation

Each of the SPR sensor cells obtained by Examples and Comparative Example was fixed to an SPR sensor (see FIG. 5).

Then, 50 µL of each of five aqueous ethylene glycol solutions having different concentrations of 1 mass % (at which a refractive index is 1.33389), 5 mass % (at which a refractive index is 1.33764), 10 mass % (at which a refractive index is 1.34245), 20 mass % (at which a refractive index is 1.35231), and 30 mass % (at which a refractive index is 1.36249) was loaded into the sample container of the SPR sensor cell. From one end of the core layers, light at a wavelength of 633 nm in Examples 1 to 16 and at a wavelength of 700 nm in Examples 17 to 25 was caused to be incident, and the intensities of light emitted from the other ends thereof were measured.

Then, transmittances (%) when the intensity of light in the absence of the aqueous ethylene glycol solutions was assumed to be 100% were determined.

Then, onto X-Y coordinates where the X-axis represents the refractive indices of the ethylene glycol solutions and the Y-axis represents the transmittances thereof, the relationships therebetween were plotted to produce analytical curves, and the absolute values of the gradients thereof and correlation factors thereof were determined. The values thereof are shown in Table 1. Note that a larger gradient shows a higher detection sensitivity, and a correlation factor closer to 1 shows a higher detection sensitivity.

TABLE 1

| | Gold-Particle-Dispersed Liquid | | | | |
|---|---|---|---|---|---|
| | Product No. | Average Particle Size | Coverage | Gradient | Correlation Factor |
| Ex. 1 | EMGC 5 | 5 nm | 40% | 121 | 0.9912 |
| Ex. 2 | EMGC 5 | 5 nm | 50% | 194 | 0.9915 |
| Ex. 3 | EMGC 5 | 5 nm | 60% | 285 | 0.9888 |
| Ex. 4 | EMGC 10 | 10 nm | 30% | 80 | 0.9910 |
| Ex. 5 | EMGC 10 | 10 nm | 40% | 144 | 0.9932 |
| Ex. 6 | EMGC 10 | 10 nm | 50% | 231 | 0.9941 |
| Ex. 7 | EMGC 10 | 10 nm | 60% | 341 | 0.9822 |
| Ex. 8 | EMGC 20 | 20 nm | 30% | 114 | 0.9905 |
| Ex. 9 | EMGC 20 | 20 nm | 40% | 206 | 0.9943 |
| Ex. 10 | EMGC 20 | 20 nm | 50% | 329 | 0.9932 |
| Ex. 11 | EMGC 20 | 20 nm | 60% | 485 | 0.9913 |
| Ex. 12 | EMGC 50 | 50 nm | 20% | 91 | 0.9904 |
| Ex. 13 | EMGC 50 | 50 nm | 30% | 195 | 0.9983 |
| Ex. 14 | EMGC 50 | 50 nm | 40% | 352 | 0.9985 |
| Ex. 15 | EMGC 50 | 50 nm | 50% | 564 | 0.9962 |
| Ex. 16 | EMGC 50 | 50 nm | 60% | 830 | 0.9887 |
| Ex. 17 | EMGC 100 | 100 nm | 30% | 116 | 0.9925 |
| Ex. 18 | EMGC 100 | 100 nm | 40% | 210 | 0.9918 |
| Ex. 19 | EMGC 100 | 100 nm | 50% | 336 | 0.9900 |
| Ex. 20 | EMGC 100 | 100 nm | 60% | 494 | 0.8777 |
| Ex. 21 | EMGC 150 | 150 nm | 40% | 90 | 0.9904 |
| Ex. 22 | EMGC 150 | 150 nm | 50% | 145 | 0.9904 |
| Ex. 23 | EMGC 150 | 150 nm | 60% | 213 | 0.8800 |
| Ex. 24 | EMGC 200 | 200 nm | 50% | 72 | 0.9900 |
| Ex. 25 | EMGC 200 | 200 nm | 60% | 106 | 0.9543 |
| Comp. Ex. | — | — | 100% | 67 | 0.9978 |

Result

In each of Examples in which the metal particle layers were formed, the gradient was larger than those in Comparative Example in which the metal thin film was formed, and the correlation factor was close to 1.

While the illustrative embodiments of the present invention are provided in the above description, such is for illustrative purpose only and it is not to be construed limitative. Modification and variation of the present invention which will be obvious to those skilled in the art is to be covered by the following claims.

INDUSTRIAL APPLICABILITY

An SPR sensor cell and an SPR sensor each according to the present invention can be used for various chemical analyses and biochemical analyses.

The invention claimed is:

1. An SPR sensor cell, comprising:
an optical waveguide to be brought into contact with a sample, wherein
the optical waveguide comprises:
an under clad layer;
a core layer provided in the under clad layer such that at least a part thereof is exposed from the under clad layer;
a metal particle layer covering the core layer exposed from the under clad layer to be brought into contact with the sample, and
an over clad layer formed on the under clad layer so as to be in a frame shape,
the over clad layer defining a sample container which contains the sample, and
the metal particle layer covering 15 to 60% of a surface area of the core layer exposed from the under clad layer in the sample container.

2. The SPR sensor cell according to claim 1, wherein an average particle size of metal particles forming the metal particle layer is in a range of 5 to 300 nm.

3. The SPR sensor cell according to claim 1, wherein the optical waveguide further comprises:
the over clad layer formed on the under clad layer so as to surround the sample in contact with the metal particle layer.

4. An SPR sensor, comprising:
an SPR sensor cell having an optical waveguide to be brought into contact with a sample, wherein
the optical waveguide comprises:
an under clad layer;
a core layer provided in the under clad layer such that at least a part thereof is exposed from the under clad layer;
a metal particle layer covering the core layer exposed from the under clad layer to be brought into contact with the sample, and
an over clad layer formed on the under clad layer so as to be in a frame shape,
the over clad layer defining a sample container which contains the sample, and
the metal particle layer covering 15 to 60% of a surface area of the core layer exposed from the under clad layer in the sample container.

* * * * *